US008189178B2

(12) United States Patent
Henning et al.

(10) Patent No.: US 8,189,178 B2
(45) Date of Patent: May 29, 2012

(54) METHOD FOR MULTI-SPECTRAL DETECTION OF AEROSOLS

(75) Inventors: Patrick F. Henning, Concord, MA (US); Aniruddha S. Weling, Framingham, CA (US); Suneet Chadha, Westford, MA (US); Jay D. Eversole, Woodbridge, VA (US)

(73) Assignee: Foster-Miller, Inc., Waltham, MA (US)

( * ) Notice: Subject to any disclaimer, the term of this patent is extended or adjusted under 35 U.S.C. 154(b) by 368 days.

(21) Appl. No.: 12/456,740

(22) Filed: Jun. 22, 2009

(65) Prior Publication Data

US 2011/0141454 A1 Jun. 16, 2011

(51) Int. Cl.
*G01J 3/00* (2006.01)

(52) U.S. Cl. ........................................ 356/51; 356/335

(58) Field of Classification Search .......... 356/335–343, 356/51

See application file for complete search history.

(56) References Cited

U.S. PATENT DOCUMENTS 6,985,818 B1 1/2006 Samuels
7,265,669 B2 * 9/2007 Call et al. ................ 340/539.26
7,295,308 B1 11/2007 Samuels
7,391,557 B1 6/2008 Bruch et al.
7,578,973 B2 * 8/2009 Call et al. ........................ 422/83
7,591,980 B2 * 9/2009 Call et al. ........................ 422/91
2005/0247868 A1 11/2005 Call et al.
2006/0066824 A1 3/2006 Knappe et al.
2008/0048129 A1 2/2008 Ting et al.
2008/0309919 A1 12/2008 Birmingham et al.

OTHER PUBLICATIONS

International Searching Authority, Written Opinion for International Application No. PCT/US2010/001777, 4 pgs. (unnumbered).

* cited by examiner

*Primary Examiner* — Layla Lauchman
(74) *Attorney, Agent, or Firm* — Iandiorio Teska & Coleman, LLP

(57) ABSTRACT

A system and method for sampling constituents in air including counting particles in the air to be sampled; collecting samples of accumulated particles; measuring UV response of a sample of accumulated particles only if the particle count exceeds a predetermined threshold; measuring IR response of that sample; and indicating a threat alarm if the IR response matches that of a target within a predetermined threshold.

22 Claims, 5 Drawing Sheets

148

METHOD FOR MULTI-SPECTRAL DETECTION OF AEROSOLS

GOVERNMENT RIGHTS

This application was made with U.S. Government support under Contract No. HSHQDC-05-C-00004 by the U.S. Department. of Homeland Security. The Government may have certain rights under the subject invention.

FIELD OF THE INVENTION

This invention relates to a system and method for detecting hazardous atmospheric constituents.

BACKGROUND OF THE INVENTION

Real-time air sampling and analysis especially to detect toxic or lethal constituents is a challenging problem. The sampling must be fast to prevent injury or even loss of life yet must be sure in order to prevent false positives which could trigger false alarms resulting in huge unnecessary displacement of people and equipment. Measuring ultraviolet (UV) fluorescence is one technique that is sensitive but is not highly accurate. Infrared (IR) absorbance is another method which is more accurate but not so fast. IR spectroscopy has greater capability to discriminate against normally occurring background clutter that sets off UV fluorescence detectors. In addition to speed and accuracy of detection continuous monitoring is also often desirable or required.

SUMMARY OF THE INVENTION

In accordance with various aspects of the subject invention in at least one embodiment the invention presents an improved aerosol sampling system and method for detecting constituents in air which is fast, accurate and reduces false positives.

The subject invention results from the realization, in part, that an improved faster, surer sampling can be achieved by counting particles in the air to be sampled and then measuring the UV fluorescence of the sample only if the particle count is above a predetermined threshold, measuring the IR absorbance of that sample and then triggering a threat alarm only if the IR spectral absorbance is matched to that of a target within a predetermined threshold, or if the UV and IR responses are both above their respective thresholds; alternatively, the IR response can be measured only if the UV fluorescence measured is above the UV fluorescence threshold and the threat alarm triggered only if the measured IR response is above the required threshold.

The subject invention, however, in other embodiments, need not achieve all these objectives and the claims hereof should not be limited to structures or methods capable of achieving these objectives.

This invention features an air sampling system for atmospheric constituents including a particle counter for counting particles present in the atmosphere, a UV detection unit, an IR detection unit, a collection apparatus for accumulating samples of particles from the air and presenting them to the UV and IR detector units, a pump system for moving air to be sampled to the particle counter and to the collection apparatus, and a controller for actuating the collection apparatus to present the sample to the UV detector unit and the IR detection unit only if the particles counted in the particle counter exceed a predetermined value, and indicating a threat alarm only if the IR detector unit and UV detector unit measure responses of the collected samples that exceed predetermined UV and IR thresholds, respectively.

In a preferred embodiment the particle counter may include a filter to exclude particles greater than a pre-selected size. The pre-selected size may be 10 microns. The collection apparatus may include a substrate for accumulating particles from air to be sampled for a predetermined duration and a mechanism for moving the substrate selectively to each of the detector units. The UV detector unit may measure UV fluorescence back-scatter in a predetermined wavelength range. The predetermined UV wavelength detector range may be 300-500 nm. The predetermined wavelength excitation range may be approximately 280-365 nm. The IR detector unit may measure IR absorption in either transmission or reflection over a predetermined wavelength range. The predetermined IR wavelength range may be 2.5-12 microns. The IR detector unit may include an IR absorption spectrometer. The collection apparatus may include an impactor for accumulating samples. The controller may actuate the collection apparatus to present a sample, first, to the UV detector unit and then to the IR detector unit only if the UV detector unit measures UV fluorescence of the sample exceeding a predetermined threshold.

The invention also features a method of sampling constituents in air including counting particles in the air to be sampled, collecting samples of accumulated particles, measuring UV response of a sample of accumulated particles only if the particle count exceeds a predetermined threshold, measuring IR spectral response of that sample, and indicating a threat alarm if the IR response matches that of a target within a predetermined threshold.

In a preferred embodiment particles larger than a predetermined size may be excluded from the counting. The predetermined size may be 10 microns. The UV fluorescence may be measured in a predetermined UV wavelength range. The predetermined wavelength range may be 300-500 nm. The IR absorbance may be measured in a predetermined IR wavelength range. The pre-selected IR wavelength range may be 2.5-12 um. The IR response may be measured by absorption spectroscopy in either reflection or transmission. The IR absorbance of the sample may be only measured if the measured UV fluorescence exceeds a predetermined threshold.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
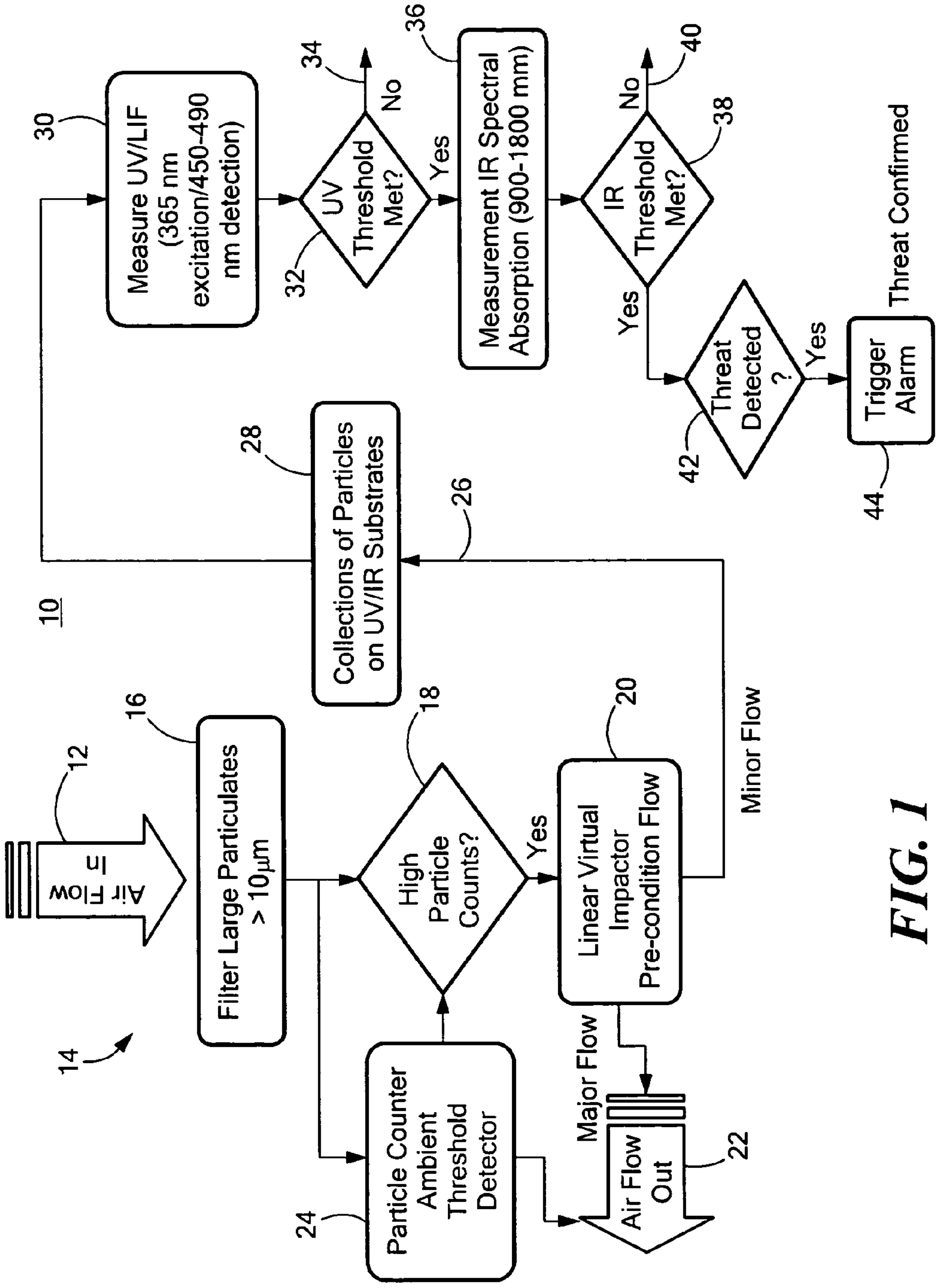
FIG. 1 is a process flow diagram of an air sampling method and system according to this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one process flow diagram 10 according to this invention, which begins with the air flow in 12 to a particle counter 14 which may include a filter 16 that filters out large particles above some size, for example 10 microns. The air is then submitted to the particle counter 18. If the particle count is below a certain level, no further action is taken; if it is above a certain level then a collection apparatus 20 is actuated. The collection apparatus may include a linear virtual impactor which receives the air on a substrate and collects particles; it also pre-concentrates particles in the correct size range. This results in a major and minor air flow. The major portion of the air flow, after passing through the linear virtual impactor or other collection apparatus, exits as indicated at the air flow out 22. There may be a particle counter ambient threshold detector 24. This is used to keep track of the ambient particle count as it varies during the day and from day to day and week to week so that the particle count at 18 can be more accurate. For example, if there were construction going on during the day in an airport where this device was installed the particulate matter in the air during the day might be very high and so the high particle count would exceed its threshold every time, which would not be an accurate representation. In that case the particle counter ambient threshold detector 24 would note a raised ambient level which can then be used to adjust the threshold high particle count. Practically, the threshold is set at some percentage of the ambient particle level. A typical count in a typical ambient condition, would be, for example, 100 particles per liter of air in the 1-10 micron size range (respirable size range). Once the collection apparatus 20 has been actuated a portion of the flow, the minor flow, is directed as indicated at 26 so that the substrate containing the sample of particles 28 is submitted now to a UV detector 30. UV detector 30 may seek to detect the fluorescence back-scatter of the particles in a particular wavelength range, for example, 300-500 nm, but it not limited to this range, with a UV excitation wavelength of, for example, 365 nm, but is not fixed at this value. If the UV fluorescence threshold for the sensitivity of the sample is not met 32 no further action may be taken as indicated at 34 and the substrates will be referred back for cleaning. The UV threshold sensitivity may be, for example some number of photons above the background response of the substrate. If the threshold is met then in this embodiment the IR spectral absorption of the particles on the sample is measured either in reflection or transmission 36. The particular IR wavelength range shown in FIG. 1 is 5.5-11 um, but the detector may operate anywhere between 2.5 and 100 um, but is not limited to this range and can be any appropriate range in the infrared spectrum. The IR threshold response for the sample particles, may be for example, based on a degree of "matching" or correlations between the sample absorption spectrum and target threat absorption spectrum, both of which are normalized/corrected so as to take amplitude or offset out of the equation. Typically, a reliable decision or correlation requires a sample of approximately 1,000 particles. If the IR threshold is not met 38, then the system may at this time take no further action as at 40 and the substrates will be referred back for cleaning. If it is met then a threat may be detected 42 and if it is a threat, an alarm is triggered 44. If no threat was detected the substrates are cleaned of all sample particles 46 and the collection apparatus returns to its quiescent state. In FIG. 1 the particle count is the first screening. If the particle count threshold is not reached then no UV detection is effected. The UV detection actually functions as a second screen for if the UV detection does not find the particle sample sensitivity to be above a certain threshold the IR spectroscopy will not occur.

Figure 2:
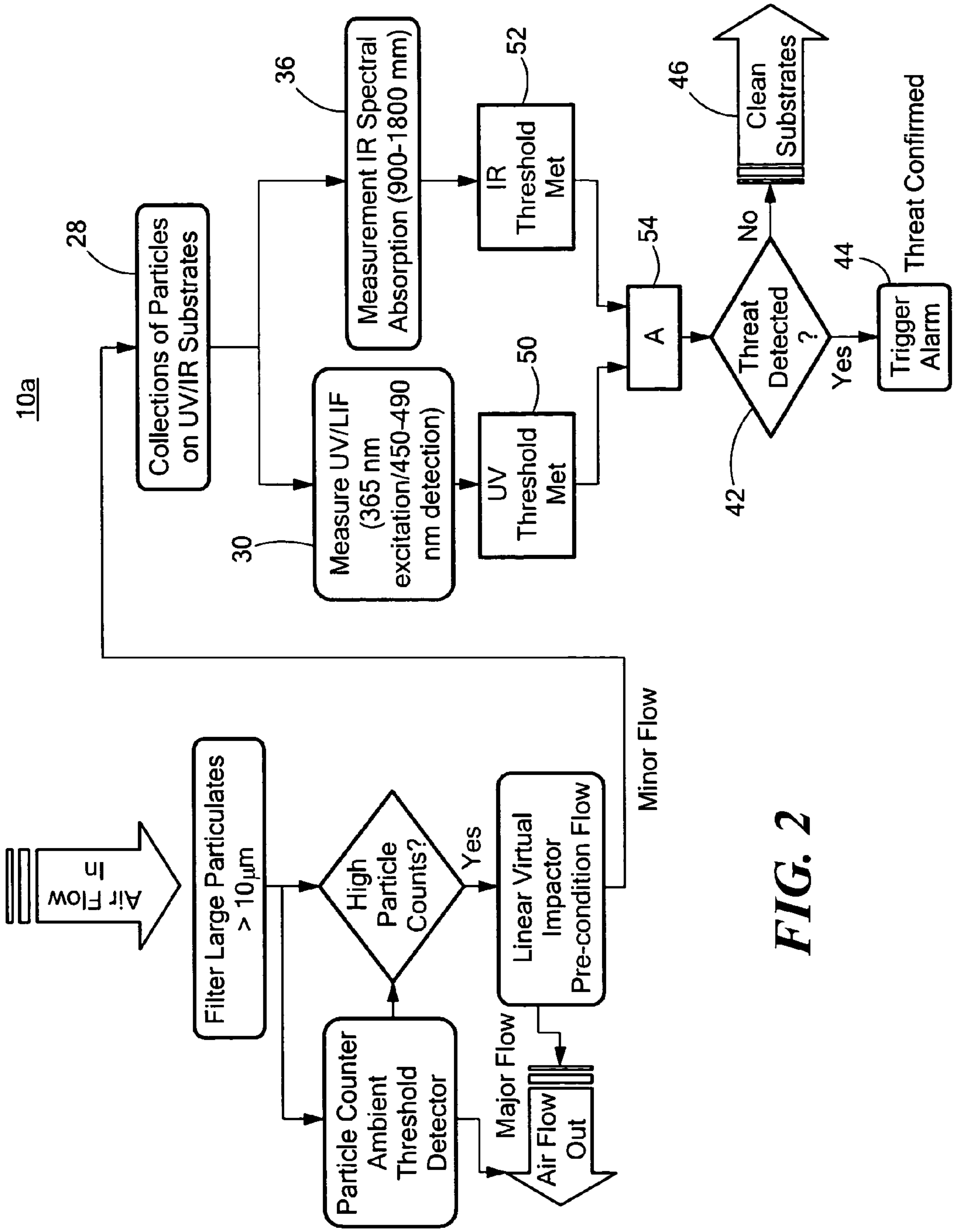
FIG. 2 is a view similar to FIG. 1 using alternative process logic.

In another embodiment, however, as shown in FIG. 2, process flow diagram 10*a* is essentially the same except for the portion following the collection of the particles 28. In flow process diagram 10*a* after the collection of the particles on the substrate 28 both the UV detection 30 and IR detection 36 are instituted simultaneously, then the output on each is checked to see whether the UV threshold 50 has been met in one case and the IR threshold 52 has been met in the other. If both thresholds have been met then AND gate 54 will pass the information to the threat detection operation 42 which will trigger a threat alarm 44. If both thresholds are not met, AND gate 54 does not provide the affirmative signal, so a threat is not detected 42, no further action is taken and the substrates will be referred for cleaning 46. A pumping system provides both the major air flow through the particle counter and the linear virtual impactor collector and the minor flow through the collection apparatus. The pumping system may include a pump for each.

Figure 3:
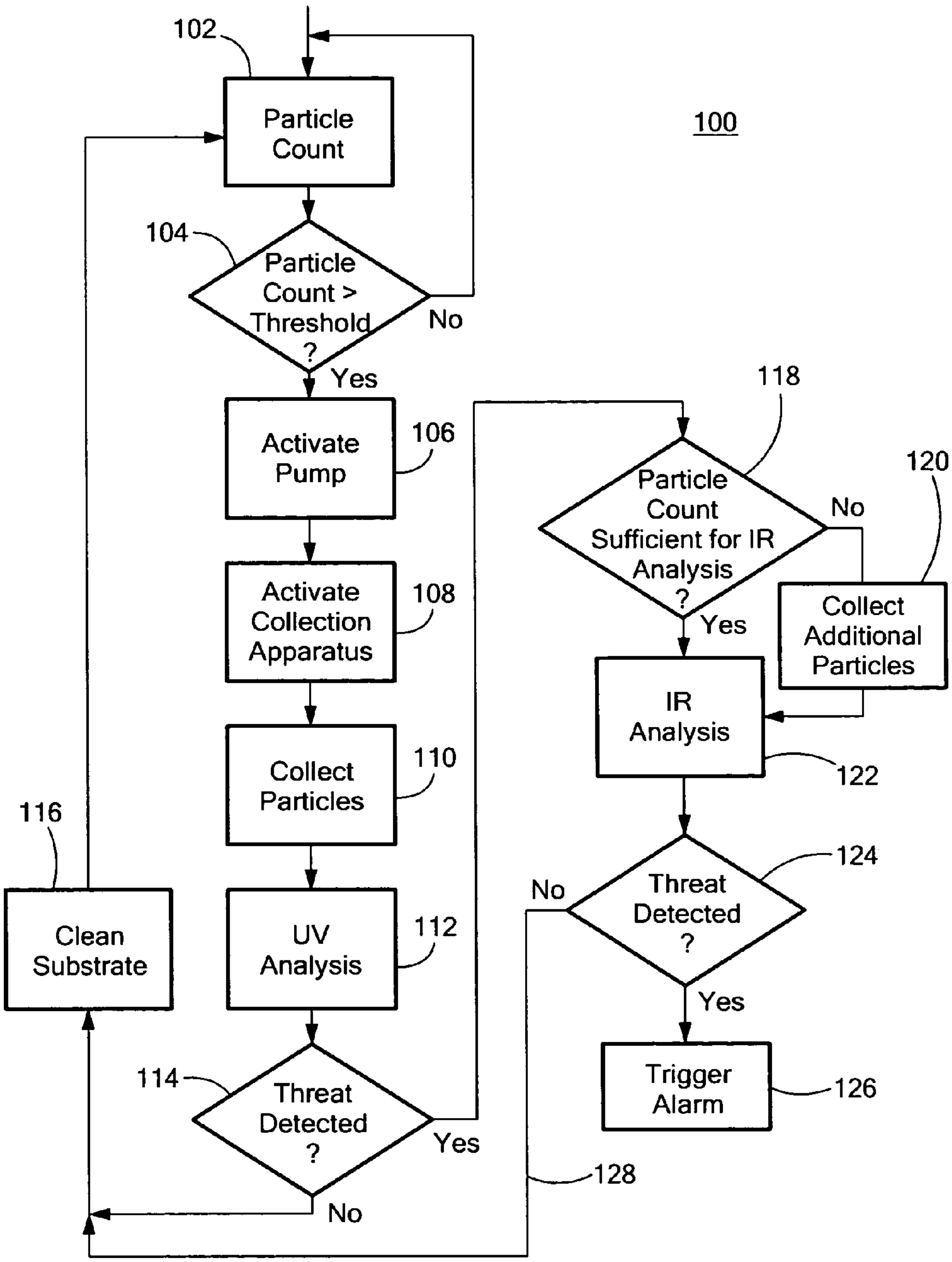
FIG. 3 is a logic flow diagram of an air sampling method according to this invention.

A flow chart 100 depicting the method of the invention is shown in the FIG. 3. This description begins with the particle count 102. If the particle count does not meet or exceed the threshold 104 the system returns to the particle count operation 102. If it does exceed the threshold a pump is actuated 106 to begin the flow to the linear virtual impactor to accumulate the sample particles on the substrate. The particle counter that does the particle counting 102 typically has its own internal pump, which is operating continuously. Once the pump is activated the collection apparatus is also actuated 108 and the particles are collected on a substrate 110. The collection apparatus then moves the substrate to a first station for UV analysis 112. If no threat is detected there 114 the substrate is cleaned 116 and referred back to the particle count operation 102. If a threat is detected then an inquiry is made as to whether the particle count is sufficient for an IR analysis 118; if not additional particles are collected 120 and then an IR analysis is done 122. If the IR analysis indicates a sensitivity of the sample particles above a certain threshold 124 then a threat alarm is triggered 126; if not the system refers on line 128 to clean the substrate 116 and return to the particle count operation 102.

Figure 4:
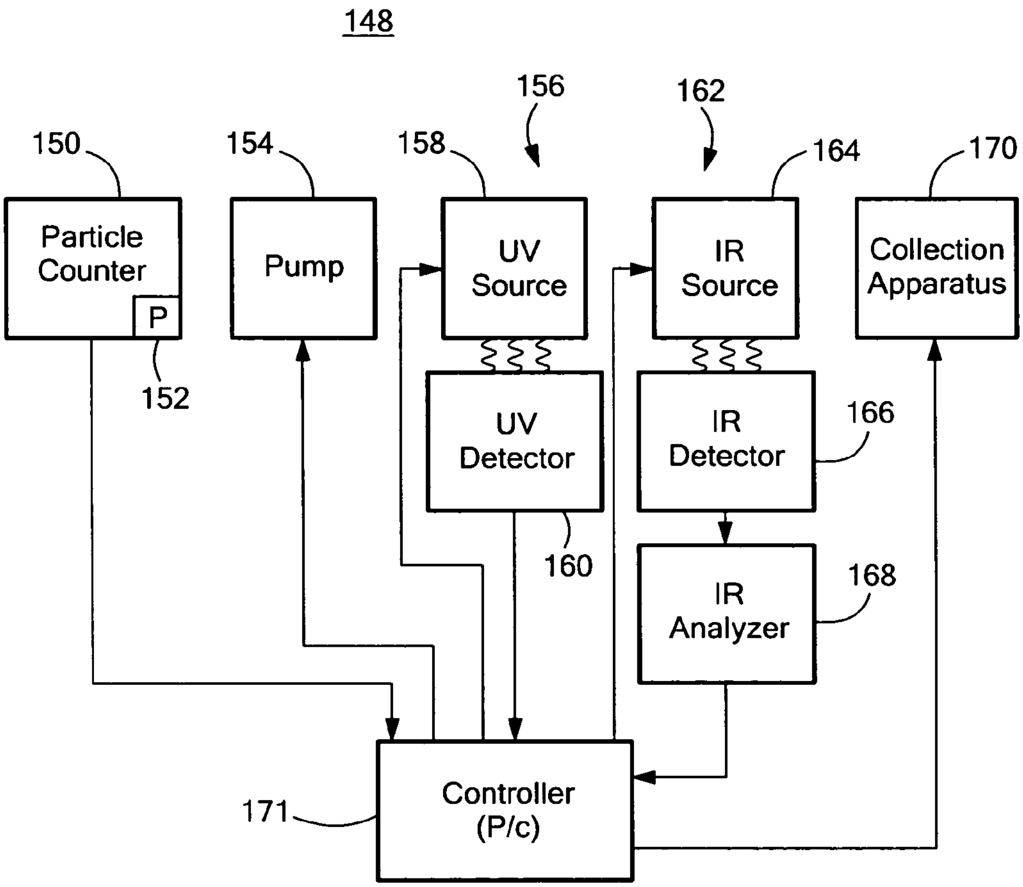
FIG. 4 is a schematic block diagram of an air sampling system according to this invention.

A schematic block diagram of the system according to this invention is shown in FIG. 4 including a particle counter 150 which has its own pump 152, a system pump 154 and a UV detector unit 156 including a UV source 158 and UV detector 160. Typically, this is a reflective detector. Also shown is the IR detector unit 162 including an IR source 164, an IR detector 166 and IR analyzer 168. The analyzer may be a spectrometer which measures sample absorbance at the desired frequencies to identify whatever contaminates or constituents the system is set to detect in aerosols. The collection apparatus 170 includes a linear actuator or other device which can move a substrate from a collection point, where, for example, the linear virtual impactor can load the sample particles onto a substrate and then the linear actuator moves the substrate to the UV detector unit 156 and the IR detector unit 162. The entire system 148 is operated by controller 171 which may be a PC, for example. Controller 171 monitors particle counter 150. If the particle count goes above a particular threshold it turns on the pump and operates collection apparatus 170 to bring a substrate in front of the impaction nozzle being supplied by pump 154, where upon a number of sample particles are collected on to the substrate from the air for a predetermined duration dependent on the inlet concentration. Controller 171 now moves collection apparatus to bring the substrate to the UV detector unit 156 and the IR detector unit 162. It monitors the output of both the UV 156 and IR 162 detector units. IF both units find a response in the sample particles above some threshold level the controller determines that a threat alarm is necessary as indicated previously with respect to FIG. 1, for example. The UV detection unit having met its threshold may be a precondition to the operation of IR detection unit 162 or they may both be operated simultaneously and a threshold-met indication from both may be required to produce a threat alarm.

Figure 5:
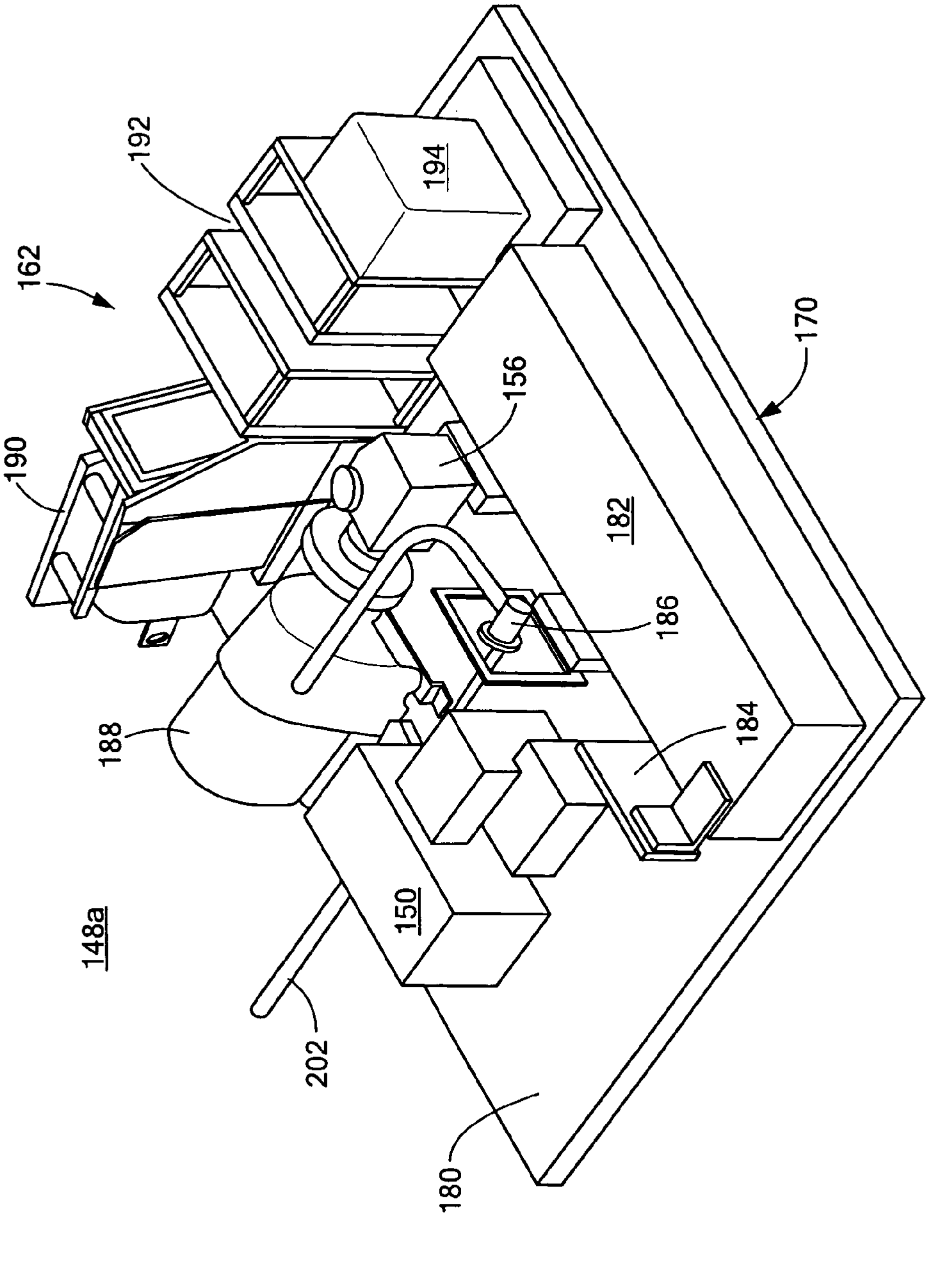
FIG. 5 is a three dimensional view of an apparatus for implementing the air sampling system according to this invention.

In one particular embodiment the system 148*a*, FIG. 5 is implemented using aerosol particle counter 150 mounted on a housing base 180 along with the other components. Particle counter 150 has an inlet 202 for inducting air and a collection apparatus 170 including linear actuator 182 which moves the substrate 184 in a removable holder from the particle deposition nozzle 186 to the UV detector unit 156 and the IR detector unit 162. An auxiliary pump 188 is provided for the minor flow while the pump 152, FIG. 4, provides the flow for the particle counter. The optical particle counter 150 flow and major flow have to be independent: the counter 150 flow is always on, while the major flow for the linear virtual impact collector is supplied by pump 154. The UV detector unit 156 includes both the source 158 and detector 160. The IR detector unit 162 includes an infrared spectrometer 190 and an infrared transmission microscope 192. The infrared source appears at 194.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. An air sampling system for atmospheric constituents comprising:

- a particle counter for counting particles present in the atmosphere;
- a UV detection unit;
- an IR detection unit;
- a collection apparatus for accumulating samples of particles from the air and presenting them to said UV and IR detector units;
- a pump system for moving air to be sampled to said particle counter and to said collection apparatus; and
- a controller for actuating said collection apparatus to present said sample to said UV detector unit and said IR detection unit only if the particles counted in the particle counter exceed a predetermined value, and indicating a threat alarm only if the IR detector unit and UV detector unit measure responses of the collected samples that exceed predetermined UV and IR thresholds, respectively.

2. The air sampling system of claim 1 in which said particle counter includes a filter to exclude particles greater than a pre-selected size.

3. The air sampling system of claim 2 in which said pre-selected size is 10 microns.

4. The air sampling system of claim 1 in which said collection apparatus includes a substrate for accumulating particles from air to be sampled for a predetermined duration and a mechanism for moving said substrate selectively to each of said detector units.

5. The air sampling system of claim 1 in which said UV detector unit measures UV fluorescence back-scatter in a predetermined wavelength range.

6. The air sampling system of claim 5 in which said predetermined UV wavelength detector range is 300-500 nm.

7. The air sampling system of claim 5 in which said predetermined wavelength excitation is approximately 280-365 nm.

8. The air sampling system of claim 1 in which said IR detector unit measures IR absorption in a predetermined wavelength range.

9. The air sampling system of claim 8 in which said predetermined IR wavelength range is 2.5-12 microns.

10. The air sampling system of claim 1 in which said IR detector unit includes an IR absorption spectrometer.

11. The air sampling system of claim 1 in which said collection apparatus includes an impactor for accumulating samples.

12. The air sampling system of claim 1 in which said controller actuates said collection apparatus to present a sample, first, to said UV detector unit and then to said IR detector unit only if the UV detector unit measures UV fluorescence of the sample exceeding a predetermined threshold.

13. A method of sampling constituents in air comprising:

- counting particles in the air to be sampled;
- collecting samples of accumulated particles;
- measuring UV response of a sample of accumulated particles only if the particle count exceeds a predetermined threshold;
- measuring IR response of that sample; and
- indicating a threat alarm if the IR response matches that of a target within a predetermined threshold.

14. The method of sampling constituents in air of claim 13 in which particles larger than a predetermined size are excluded from the counting.

15. The method of sampling constituents in air of claim 14 in which the predetermined size is 10 microns.

16. The method of sampling constituents in air of claim 13 in which the UV fluorescence is measured in a predetermined UV wavelength range.

17. The method of sampling constituents in air of claim 16 in which the predetermined wavelength range is 300-500 nm.

18. The method of sampling constituents in air of claim 13 in which the IR absorbance is measured in a predetermined IR wavelength range.

19. The method of sampling constituents in air of claim 18 in which the pre-selected IR wavelength range is 2.5-12 um.

20. The method of sampling constituents in air of claim 13 in which the IR response is measured by absorption spectroscopy.

21. The method of sampling constituents in air of claim 13 in which the IR absorbance of the sample is only measured if the measured UV fluorescence exceeds a predetermined threshold.

22. The air sampling system of claim 1 in which said controller indicates the threat alarm only if the IR response exceeds the predetermined IR threshold.

* * * * *

UNITED STATES PATENT AND TRADEMARK OFFICE

CERTIFICATE OF CORRECTION

PATENT NO. : 8,189,178 B2
APPLICATION NO. : 12/456740
DATED : May 29, 2012
INVENTOR(S) : Patrick Henning et al.

It is certified that error appears in the above-identified patent and that said Letters Patent is hereby corrected as shown below:

On The Title Page, Item (75) Inventors listed should read --

Patrick Henning, Concord, MA (US);
Aniruddha Weling, Framingham, CA (US)
Suneet Chadha, Westford, MA (US)
Jay Eversole, Woodbridge, VA (US)
Horn-Bond Lin, Las Vegas, NV (US)
Cathy Simpson Scotto, Montclair, VA (US)

Signed and Sealed this
Nineteenth Day of May, 2015

Michelle K. Lee
*Director of the United States Patent and Trademark Office*